United States Patent
Harley

[11] Patent Number: 5,237,386
[45] Date of Patent: Aug. 17, 1993

[54] OPTICAL COUPLING ARRANGEMENT FOR PARTICULATE DETECTOR

[75] Inventor: Phillip E. Harley, Jesmond, England

[73] Assignee: Kidde-Graviner Limited, Derby, England

[21] Appl. No.: 761,819

[22] PCT Filed: Mar. 16, 1990

[86] PCT No.: PCT/GB90/00402
§ 371 Date: Sep. 20, 1991
§ 102(e) Date: Sep. 20, 1991

[87] PCT Pub. No.: WO90/11508
PCT Pub. Date: Oct. 4, 1990

[30] Foreign Application Priority Data
Mar. 22, 1989 [GB] United Kingdom ............ 8906554

[51] Int. Cl.⁵ .......................................... G01N 21/49
[52] U.S. Cl. ................................. 356/338; 250/574; 250/227.11; 356/339
[58] Field of Search ............ 356/336, 338, 339, 237; 250/227.11, 574, 227.2, 573, 576; 385/12, 124

[56] References Cited
U.S. PATENT DOCUMENTS

| | | | |
|---|---|---|---|
| 2,892,378 | 6/1959 | Canada | 356/339 X |
| 3,141,094 | 7/1964 | Strickler | 356/440 X |
| 3,593,026 | 7/1971 | Uchida et al. | 250/227.11 X |
| 4,328,488 | 5/1982 | Yanai et al. | 385/12 X |
| 4,752,131 | 6/1988 | Eisenlauer et al. | 356/338 |
| 4,799,756 | 1/1989 | Hirschfeld | 385/12 X |
| 4,859,864 | 8/1989 | Smith | 356/436 X |
| 4,896,048 | 1/1990 | Borden | 356/339 X |

FOREIGN PATENT DOCUMENTS

| | | | |
|---|---|---|---|
| 69968/81 | 5/1986 | Australia. | |
| 60-128331 | 7/1985 | Japan | 356/338 |
| 1-47936 | 2/1989 | Japan | 250/227.11 |

*Primary Examiner*—Vincent P. McGraw
*Attorney, Agent, or Firm*—Leydig, Voit & Mayer

[57] ABSTRACT

Apparatus for detecting particulates (46) within a medium in a chamber (10) comprises a photo-detector (14) which is maintained at a stable low temperature by a Peltier type cooling device (42). Scattered light from the particulate (46) is focused by a spherical lens (34) onto the input face (30) of a rod lens (22). The latter has an optical pitch of 0.5 and transfers the image to its output face (25) whence it passes via a light pipe (18) to the sensitive area (16) of the photo-electric device (14). The rod lens (22) provides an inexpensive means for transferring the light and which provides a thermal barrier. Thus, although the photo-electric device (14) is held at a low temperature, the input face (30) of the rod lens (22) can be held at the temperature of the medium within the chamber (10) and is not subjected to the formation of mist or ice. The lens (34) is mounted by means of a collar (28) which is slidable into a position in which the lens (34) focuses the input light into the face (30) of the lens (22), and then secured in this position by ultra-violet-cured adhesive fillets (32, 34).

17 Claims, 2 Drawing Sheets

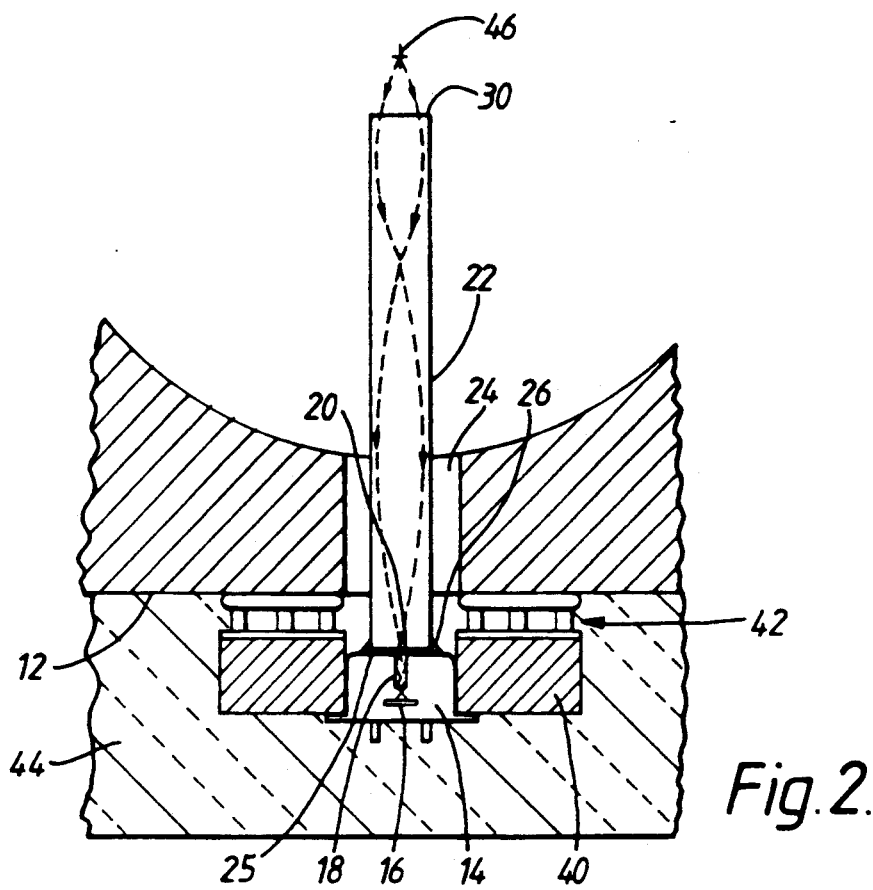
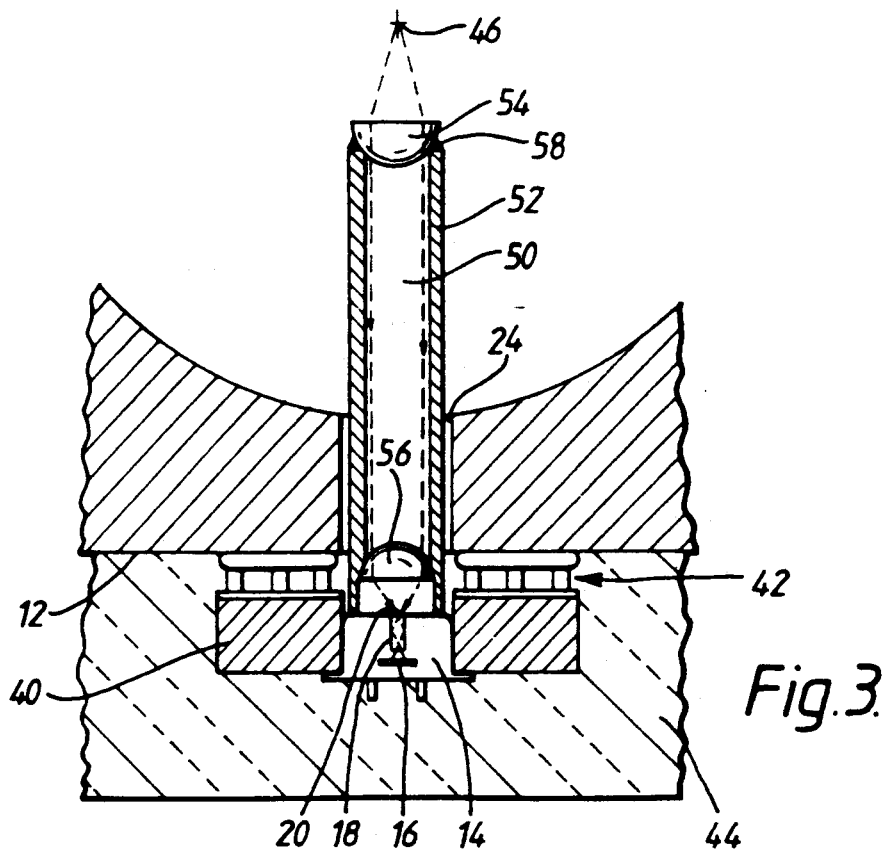

OPTICAL COUPLING ARRANGEMENT FOR PARTICULATE DETECTOR

BACKGROUND OF THE INVENTION

The invention relates to particulate detecting and optical coupling arrangements. One such arrangement may be used within a system intended for sensing the presence of particulates within a gaseous or liquid medium; the medium is illuminated and the light scattered by any particulates present in the medium is collected by the optical coupling arrangement and transferred to a suitable photo-detecting device.

SUMMARY OF THE INVENTION

According to the invention, there is provided a particulate detecting arrangement, comprising light directing means for directing a beam of light into an area in which particulates may be present whereby the light is scattered by any such particulates, and light detecting means positioned to receive such scattered light and to respond to it and to detect it, characterised in that the light directing means is a laser and the light detecting means is an avalanching photo-diode.

According to the invention, there is also provided an optical coupling arrangement for collecting light present within a predetermined area as a result of the presence of particulates therein and for coupling the said light to light detecting means, characterised by an elongate optical member having a longitudinal dimension substantially greater that its transverse direction and extending longitudinally into the enclosure from wall means thereof and adapted to receive the said light and to transmit it to and to focus it onto the said light detecting means situated outside the enclosure.

According to the invention, there is further provided an optical coupling arrangement for focussing light onto light detecting means, characterised by lens means providing a thermal barrier.

DESCRIPTION OF THE DRAWINGS

Particulate detecting and optical coupling arrangements embodying the invention will now be described, by way of example only, with reference to the accompanying diagrammatic drawings in which:

FIG. 2 is a partial cross-section through another of the arrangements; and

FIG. 3 is a partial cross-section through a further one of the arrangements.

DESCRIPTION OF PREFERRED EMBODIMENTS

Figure 1:
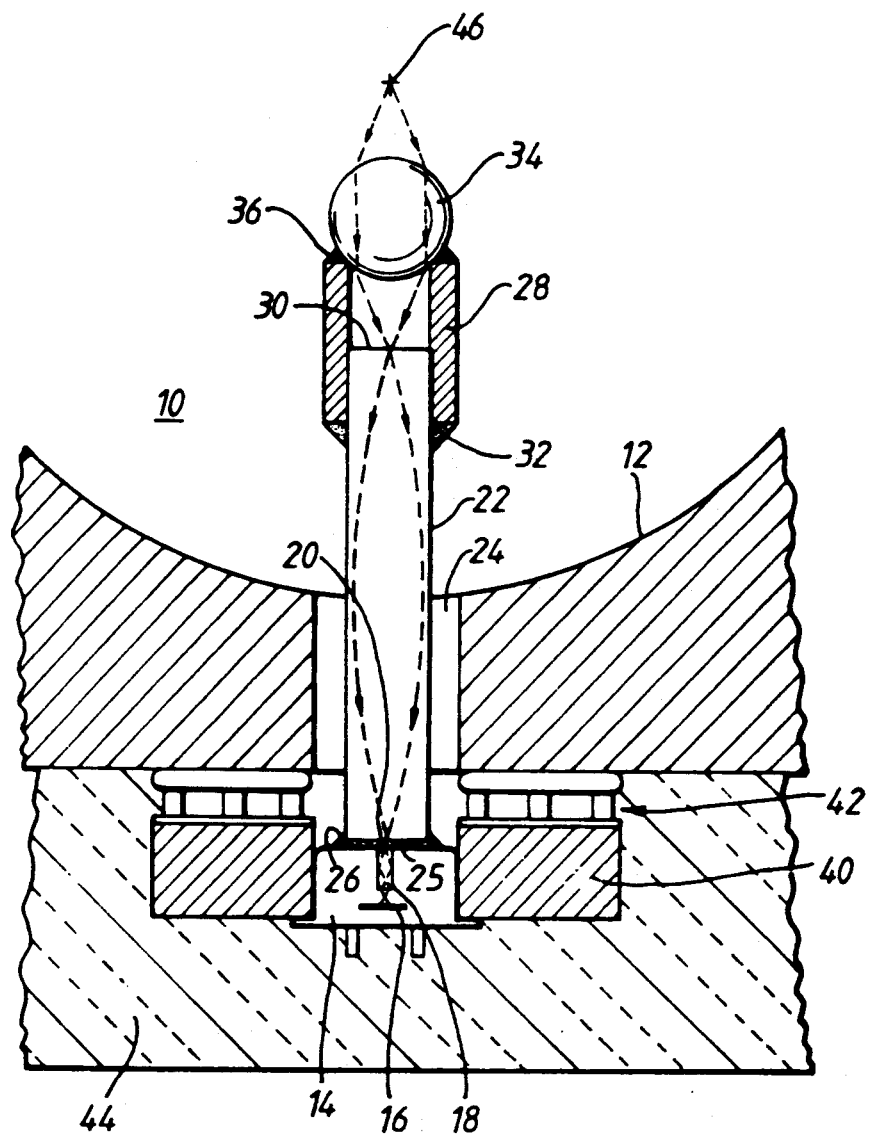
FIG. 1 is a partial cross-section through one of the arrangements.

The arrangement of FIG. 1 incorporates a chamber 10, part of whose wall is shown at 12, in which flows the medium in which the presence of particulates is to be sensed. The medium may be gaseous or liquid. A light source (not shown), preferably a laser beam, illuminates the medium within the chamber 10. Any particulates present within the medium will scatter the impinging light and the purpose of the optical coupling arrangement to be described is to collect the scattered light and to detect it by means of a photo-detector, thereby indicating the presence of the particulates.

The photo-detector is shown generally at 14 and comprises, in this example, an avalanche-type photo-detector. The sensitive area of the detector 14 is shown at 16 and it incorporates an integral light pipe 18 which conducts light from its face 20 to the sensitive area 16.

The optical coupling arrangement includes a graded index rod lens 22 which extends through a bore 24 in the wall 12 of the chamber 10 and has a face 25 which is optically coupled to the light pipe 18 and the face 20 of the photo-detector by means of a UV-cured adhesive 26. The rod lens 22 extends well into the chamber 10 and has a metal collar 28 attached adjacent its inner face 30 by means of UV-cured adhesive 32. The metal collar 28 supports a lens 34 which is in the form of a complete sphere and which is attached to the collar 28 by means of further UV-cured adhesive 36.

The photo-detector 14 has to be maintained at a stable temperature for effective operation. For this purpose, the detector is mounted within a metal block 40 and a Peltier-type solid state cooling device 42 is sandwiched between this block 40 and the wall 12 of the chamber. The Peltier device acts as a heat pump, collecting heat from the block 40 and the photo-detector 14 and transferring it to the wall 12 of the chamber which is designed to act as a heat sink. The temperature of the Photo-detector 14 is maintained stably at a relatively low value, minus 5C in this example. In order to assist in this, the photo-detector 14, the metal block 40 and the Peltier device 42 are enclosed within thermally insulating foam 44.

Instead, the temperature of the photo-detector could be stably maintained at a temperature corresponding to normal ambient temperature by some other suitable temperature control device.

In operation, light scattered by a particulate shown diagrammatically at 46 is imaged by the lens 34 onto the face 30 of the rod lens 22. The rod lens has an optical pitch equal to 0.5, so that the image received at its inner face 30 is transferred to its outer face 25 where the light exits and passes into the light pipe 18 and thus onto the sensitive area 16 of the detector 14 which thus detects it.

The UV-cured adhesive fillets 26,32 and 36 provide optical gating in addition to structural attachment. The position of the metal collar 28 on the lens 22 is adjusted, before curing the adhesive, so as to provide correct focussing of the light onto the face 30 of the rod lens.

The rod lens 22 has low thermal conductivity and provides a thermal barrier within the optical path. Therefore, although its outer face 25 is cooled, by being in close proximity to the cooled detector 14, its inner face 30, being immersed in the medium within the sensing chamber 10, will be at the temperature of the medium. Assuming, as will normally be the case, that this medium is at a reasonably elevated temperature, the face 30 will therefore not attract moisture or ice formations. Furthermore, fluctuations in temperature at the face 30, caused by changes in temperature in the medium, are not, or are only slightly, transmitted to the face 25, thus minimising the demands on the temperature control device.

If the photo detector used does not have its own in-built light pipe (corresponding to the light Pipe 18), the rod lens 22 will be arranged to have an optical pitch less than 0.5 so as to transfer the image form its inner face 30 directly to the sensitive area of the detector.

The lens 34 can be a standard type of lens used for coupling optical fibers, such lenses being widely available and relatively inexpensive.

In the arrangement shown in FIG. 2, items corresponding to those in FIG. 1 are correspondingly referenced.

The arrangement in FIG. 2 differs from that of FIG. 1 in that the arrangement of FIG. 2 does not incorporate the spherical lens 34 or its supporting collar 28. In this arrangement, the light scattered by the particulate 46 is directly collected by the face 30 at the end of the graded index rod lens 22. The optical pitch of the graded index rod lens is selected so that it focuses light received from the particulate onto the face 20 of the detector 14. In this example, the optical pitch of the rod lens is approximately 0.85. However, it could have any other value, for example less than 0.5, which is suited to its length and such as to ensure that the light is focused onto the detector 14.

In the arrangement shown in FIG. 3, items corresponding to those in FIGS. 1 and 2 are again similarly referenced.

In the arrangement of FIG. 3, a graded index rod lens is not used. Instead, a support tube 50 extends through the bore 24 in the wall 12 and terminates adjacent to the photo detector 14. Collection of light scattered from the particulate 46, and focussing of this light onto the photo detector 14, is carried out by means of micro lenses 54 and 56. Each of these lenses is a converging lens such as a plano-convex lens. Lens 54 is attached to the outer end of the tube 50 by ultra-violet cured adhesive 58 and collects the scattered light and passes it into the tube 50. Lens 56 is also converging, such as plano-convex and receives the light transmitted and focuses it onto the photo detector 14.

Although the arrangement of FIG. 3 does not use a graded index rod lens, the tube 50 which it uses instead also acts as a thermal barrier so that fluctuations in temperature in the vicinity of the lens 54 are not, or are only slightly, transmitted to the area of the photo detector, thus minimising the demands on the temperature control device of the photo-detector.

The arrangements described provide simple (and particularly in the case of the FIG. 1 and 2 arrangements) inexpensive methods of collecting very weak light levels scattered from particulates in gaseous or liquid media, and have the advantage of maximising the solid angle of collection. This is at least partially achieved by the types of construction illustrated which use an elongate optical member (the graded index rod lens 22 or the tube 50) which extends substantially into the enclosure from the wall thereof. The arrangements avoid the use of large lenses. They also provide a thermal barrier within the optical path, thus blocking temperature fluctuation in the medium from being transmitted to and adversely affecting the operation of the photo-detector.

The systems described may advantageously be designed to operate in a sampling mode. The enclosure 10 becomes a Pipe into which a sample of the medium to be tested for particulates is drawn.

I claim:

1. An optical coupling arrangement, comprising
an elongate optical coupling member extending from an input end to an output end with a longitudinal dimension substantially greater than its transverse dimension and incorporating lens means operative at each said end,
an enclosure defined by wall means,
the elongate optical coupling member protruding longitudinally into the enclosure from an inside surface of the wall means so as to extend into and be actually situated in a predetermined volume within the enclosure which may contain particulates,
a separate light source directing light into the said volume so that the input end of the optical coupling member collects any of the said light which is scattered by the particulates in the enclosure,
the output end of the coupling member being positioned outside the enclosure, and
light detecting means positioned at the output end of the coupling member so that the optical coupling member couples the collected light to the light detecting means.

2. An arrangement according to claim 1, in which the elongate optical coupling member additionally provides a thermal barrier between the interior of the enclosure and he light detecting means.

3. An arrangement according to claim 1, including means for repeatedly drawing into the said volume respective samples of a medium in which the said particulates may be present.

4. An arrangement according to claim 1,
in which the elongate optical member comprises a graded index rod lens.

5. An arrangement according to claim 4, including means supporting the output end of the rod lens in optical coupling with the light detecting means, and in which the optical pitch of the rod lens is dimensioned to focus he light received at its input end on to the light detecting means, the input end of the rod lens being positioned at the input end of the optical coupling member.

6. An arrangement according to claim 5, including means supporting the output end of the rod lens in optical coupling with the light detecting means, and in which the lens means operative at the input end of the optical coupling member comprises a further lens for receiving the light and focussing it onto the input end of the rod lens, the optical pitch of the rod lens being chosen to focus the image received at its input end onto the light detecting means.

7. An arrangement according to claim 6, in which the further lens is a spherical lens.

8. An arrangement according to claim 7, in which the spherical lens is mounted adjacent the input end of the rod lens by means of a supporting collar slidable telescopically with respect to the rod lens into a position providing correct focussing, and means securing the collar in the said position.

9. An arrangement according to claim 8, in which the means securing the collar in the said position comprises ultra-violet curd adhesive.

10. An arrangement according to claim 4, including ultra-violet cured adhesive securing the output end of the rod lens to the light detecting means.

11. An arrangement according to claim 1, in which the elongate optical member comprises elongate light transmitting means for receiving the light and transmitting it to the light detecting means, and lens means at its input and output ends and adapted to focus the transmitted light onto the light detecting means.

12. An arrangement according to claim 11, in which the lens means comprises a converging lens positioned at the output end of the light transmitting means between the light transmitting means and the light detecting means and a second converging lens positioned at the input end of the light transmitting means to collect the said light in the enclosure and feed it into the light transmitting means.

13. An arrangement according to claim 1, in which the light originates form a laser and in which the light detecting means is an avalanching photo-diode.

14. An arrangement according to claim 1, including a temperature control device for maintaining the light detecting means substantially at a predetermined temperature.

15. An arrangement according to claim 14, including a metal enclosure adjacent to the light detecting means, and in which the temperature control device comprises cooling means for extracting heat from this metal enclosure and transmitting it to a heat sink.

16. An arrangement according to claim 15, in which the heat sink comprises the wall of the enclosure.

17. An arrangement according to claim 16, in which the cooling means is a Peltier cooling device.

* * * * *